United States Patent

Geiss et al.

[11] Patent Number: 5,102,892
[45] Date of Patent: Apr. 7, 1992

[54] 2-ALKYL-4-ARYLMETHYLAMINOQUINOLINES, THE USE THEREOF AND DRUGS PREPARED THEREFROM

[75] Inventors: Karl-Heinz Geiss, Heuchelheim; Klaus Ruebsamen, Neustadt; Martin Traut, Heidelberg, all of Fed. Rep. of Germany

[73] Assignee: BASF Aktiengesellschaft, Ludwigshafen, Fed. Rep. of Germany

[21] Appl. No.: 486,824

[22] Filed: Mar. 1, 1990

[30] Foreign Application Priority Data

Mar. 17, 1989 [DE] Fed. Rep. of Germany ....... 3908767
Dec. 28, 1989 [DE] Fed. Rep. of Germany ....... 3943158

[51] Int. Cl.$^5$ .................. A61K 31/47; C07D 215/42
[52] U.S. Cl. ................................. 514/313; 546/156; 546/159; 546/170
[58] Field of Search ................ 546/159; 514/313

[56] References Cited

U.S. PATENT DOCUMENTS

| 3,075,984 | 1/1963 | Surrey ................... 546/159 |
| 4,343,804 | 8/1982 | Munson, Jr. et al. ........... 546/159 |
| 4,744,823 | 5/1988 | Raymond-Seraille ............ 75/68 R |

FOREIGN PATENT DOCUMENTS

| 0258755 | 3/1988 | European Pat. Off. . |
| 0259174 | 3/1988 | European Pat. Off. . |
| 0307078 | 3/1989 | European Pat. Off. . |
| 0322133 | 6/1989 | European Pat. Off. . |
| 0326328 | 8/1989 | European Pat. Off. . |
| 326331  | 8/1989 | European Pat. Off. ............ 546/159 |
| 0334491 | 9/1989 | European Pat. Off. . |
| 0336544 | 10/1989 | European Pat. Off. . |
| 0339768 | 11/1989 | European Pat. Off. . |
| 0342775 | 11/1989 | European Pat. Off. . |
| 1496371 | 12/1977 | United Kingdom . |

OTHER PUBLICATIONS

Dreikorn et al., vol. 112, No. 55630 (Abstract for EP 326331, Aug. 2, 1989.)
J. Indian Chem. Soc., vol. 51, Oct. 1974, pp. 880-882; Mukhopadhyay et al., "Synthesis of Possible Antiamebic Agents".
J. Indian Chem. Soc., vol. 56, Jul. 1979, pp. 651-655; "Interaction of Cobalt(II) Schiff Base Complexes ...".
Ann. of Biochem. and Experimental Med., vol. 20, 1960, Supplement, pp. 493-504, Kaushiva: "Antiamoebic Action of Substuted ...".
J. of Scient. & Ind. Research, vol. 13B, No. 1, Jan. 1954, pp. 15-20, Golpalchari et al: "Studies in Potential Amoebicides ...".
Bull. Soc. Chimique de France, 1973, pp. 2860-2864, Berlot et al.: "Alkylation en milieu neutre par les carbures ...".
C. R. Acad. Sc. Paris, Ser. C 275 (1972), pp. 1041-1044, Berlot et al.: "Alkylation en milieu neutre de quelques ...".

*Primary Examiner*—Mukund J. Shah
*Assistant Examiner*—E. Bernhardt
*Attorney, Agent, or Firm*—Oblon, Spivak, McClelland, Maier & Neustadt

[57] ABSTRACT

2-alkyl-4-arylmethylaminoquinolines of the general formula I

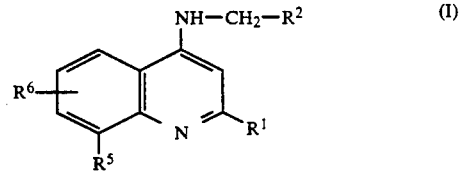

where $R^1$, $R^2$, $R^5$ and $R^6$ have the meanings specified in the claims, and the physiologically tolerated salts thereof, the use thereof for the preparation of drugs and the drugs thus obtained as described for the inhibition of gastric acid secretion.

7 Claims, No Drawings

2-ALKYL-4-ARYLMETHYLAMINOQUINOLINES, THE USE THEREOF AND DRUGS PREPARED THEREFROM

The present invention relates to novel 2-alkyl-4-arylmethylaminoquinolines and the use thereof for controlling diseases.

The following citations have described 8-substituted 4-benzylamino-2-methylquinolines with potential amebicidal and, in some cases, fungicidal actions: J. Indian Chem. Soc. 51 (1974), 880–882 J. Indian Chem. Soc. 56 (1979), 1265–1268 Ann. Biochem. Exptl. Med. (Calcutta) Suppl. 20 (1960) 493–504 (=CA-58, 8254c) J. Scient. Ind. Res. India 13B (1954), 15–21.

4-Arylmethylaminoquinolines with fungicidal activity are described in EP 326,328.

In a general form, 2-alkyl-4-benzylaminoquinolines have been mentioned as intermediates in U.S. Pat. No. 3,075,984; 2,8-dimethyl-4-benzylaminoquinoline has been described in Bull. Soc. Chim. France 1973, 2860–2864 and in C. R. Acad. Sci., Ser. C 275 (1972), 1041–1044. However, no pharmacological actions have been described for these compounds.

The following may be mentioned from the wider field of pharmacologically active 4-aminoquinolines with great variation in the substitution pattern on the quinoline structure:

2-unsubstituted 4-anilino- and 4-phenylalkylaminoquinolin-3-yl ketones and carboxylates which act to inhibit secretion of gastric acid have been described in U.S. Pat. No. 4,343,804 and in EP-A 259 174.

EP-A 258 755 claimed 4-amino-2-methylquinolin-3-yl ketones and -alkanols for the treatment of Alzheimer's disease.

We have now found, surprisingly, that the compounds of the formula I according to the invention

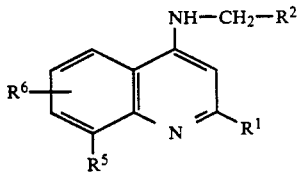

where
$R^1$ is $C_1$–$D_3$-alkyl which can be substituted by hydroxyl or $C_1$–$C_3$-alkoxy,
$R^2$ is either naphthyl or a radical of the formula (a)

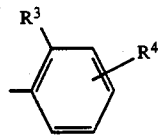

where
$R^3$ is $C_1$–$C_3$-alkyl which can be substituted by hydroxyl or methoxy, or is $C_1$–$C_3$-alkoxy, fluorine, chlorine or bromine, and
$R^4$ is hydrogen, methyl, hydroxy, methoxy, fluorine, chlorine or bromine, and
$R^5$ is $C_1$–$C_3$-alkoxy, $C_1$–$C_3$-alkoxy which can be substituted by hydroxyl or $C_1$–$C_3$-alkoxy, or is hydroxyl, fluorine, chlorine or bromine, and
$R^6$ is hydrogen, methyl, methoxy, fluorine, chlorine or bromine, and the physiologically tolerated salts thereof have valuable pharmacological actions. In particular, they inhibit K/H ATPase and the acid secretion of the stomach.

$R^1$ is preferably methyl which can be substituted by hydroxyl or $C_1$–$C_3$-alkoxy, in particular methoxy.

$R^2$ is preferably 1-naphthyl or a radical of the formula (a).

$R^3$ is preferably $C_1$–$C_3$-alkyl, in particular methyl or ethyl, $C_1$–$C_3$-alkoxy, in particular methoxy, or chlorine or bromine.

$R^4$ is preferably hydrogen, 4-hydroxy, 6-methyl, 6-methoxy, 6-fluoro or chloro, in particular hydrogen or 6-fluoro or 6-chloro.

$R^5$ is preferably $C_1$–$C_2$-alkoxy, or $C_1$–$C_2$-alkyl which can be substituted by hydroxyl or methoxy. $R^5$ is particularly preferably methoxy, methyl or ethyl.

$R^6$ is preferably hydrogen.

The compounds according to the invention are prepared in a conventional manner by reacting a quinoline of the formula II

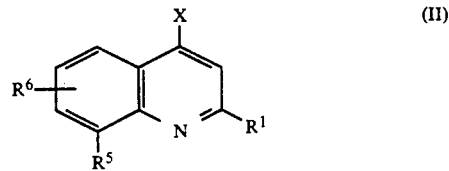

where X is a nucleophilic leaving group such as chlorine or bromine or phenoxy, and $R^1$, $R^5$ and $R^6$ have the above meanings, with an amine of the formula $R^2$—$CH_2$—$NH_2$ in a conventional manner.

The reaction can be carried out in the presence of a solvent such as toluene, xylene, phenol, ethanol, dimethyl sulfoxide, dimethylethyleneurea, dimethylpropyleneurea, pyrrolidone or N-methylpyrrolidone, in mixtures of these solvents or in the absence of a solvent, in the presence or absence of a catalyst such as copper or bronze powder or copper (I) chloride at from 50 to 250° C., under atmospheric or superatmospheric pressure. The amines $R^2CH_2NH_2$ can be employed in equimolar amounts or in excess.

The reaction of the compounds of the formula II with the amines $R^2CH_2NH_2$ is preferably carried out in the ration 1:1 to 1:10 in the presence of phenol at from 60 to 160° C.

The preparation of 4-aminoquinolines by the above process has been described in the following citations, inter alia: G. Jones, Quinolines, Part I, John Wiler & Sons, London, New York, 1977, pp. 547–550 and literature cited therein; J. Indian Chem. Soc. 51 (1974) 880–882; J. Med. Chem. 14 (1971) 1060–1066; Chim. Therap. 1 (1966) 339–346; Eur. J. Med. Chem. 11 (1976) 561–565.

The amines $R^2CH_2NH_2$ and the precursors of the formula II are known from the literature or commercially available, or can be prepared in a similar manner to known compounds.

For the preparation of 4-chloro-, 4-bromo- and 4-phenoxyquinolines, see G. Jones (Ed.) Quinolines, part I, John Wiler & Sons, London, 1977: X=Cl: pp. 391–398; X=Br: pp 404–406; X=OC$_6$H$_5$: pp. 577–579. 4-Phenoxyquinolines can also be detected as intermediate in the reaction of 4-chloroquinolines with amine $R^2CH_2NH_2$ in the presence of phenol.

For the preparation of the compound II, X=Cl, $R^1$=CH$_3$, $R^5$=OCH$_3$, $R^6$=H (CA Reg. No. 64 951-58-2), see, for example, Coll. Czech. Chem. Com. 20 (1955) 1206-1214; J. Chem. Soc. 1932, 1984-1988.

The compounds of the formula I according to the invention in which $R^1$ is hydroxymethyl can also be obtained by reduction of compounds of the general formula III

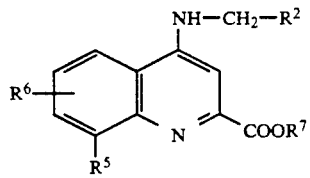

where $R^2$, $R^5$ and $R^6$ have the meanings mentioned for formula I, and $R^7$ is hydrogen or $C_1$-$C_3$-alkyl, with suitable reducing agents such as lithium aluminum hydride.

The compound of the formula I according to the invention in which $R^1$ is $C_1$-$C_3$-alkoxymethyl can also be obtained by reacting the compounds of the formula IV

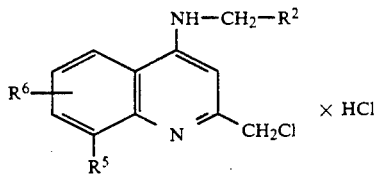

where $R^2$, $R^5$ and $R^6$ have the said meanings, with an alkali metal $C_1$-$C_3$-alkoxide in a solvent such as the corresponding $C_1$-$C_3$-alcohol or dimethylformamide.

The precursors of the formula IV can be prepared by reacting compounds of the formula I where $R^1$ denotes hydroxymethyl with thionyl chloride: One hydroxyl group in $R^5$ must be provided with a suitable protective group which is eliminated again after the reaction of the compounds IV with $C_1$-$C_3$-alkoxides to give compounds I, $R^1$ =CH$_3$O-C$_1$-C$_3$-alk.

The precursors of the formula III can be obtained by reacting compounds of the formula V

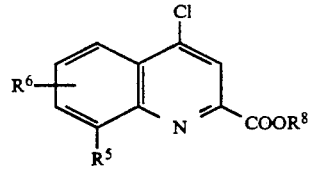

where $R^8$ is $C_1$-$C_4$-alkyl, with amines of the formula $R^2CH_2NH_2$ by the process described for the reaction of compounds II with the amines $R^2CH_2NH_2$, it being possible for the esters (III, $R^7$=C$_1$-C$_3$-alkyl) then to be hydrolyzed to the carboxylic acids (III, $R^7$=H).

The precursors of the formula V can be obtained by reacting the 4-hydroxyquinolines of the formula VI

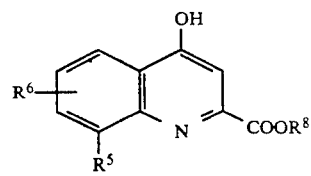

where $R^8$ has the meaning mentioned for formula V, with conventional chlorinating agents such as POCl$_3$, Cl$_5$ or SOCl$_2$, with one hydroxy group in $R^5$ first being provided with a suitable protective group which is eliminated again after the reaction to give compounds of the formula V has taken place. For the preparation of compounds of the formula VI, $R^6$=H, see, for example, J. Org. Chem. 16 (1951) 412-414; J. Amer. Chem. Soc. 73 (1951) 3520; Z. Naturforsch. 35B (1980) 1569-1571; Z. Physiol. Chem. 297 (1954) 247-248.

The compounds obtained according to the invention can be converted into the acid addition salt of a physiologically tolerated acid. A list of conventional physiologically tolerated acids is to be found in Fortschritte der Arzneimittelforschung 1966, Deutschland, Schweiz, Birkhäuser Verlag, vol. 10, pp. 224-285 and J. Pharm. Sci. 66 (1977), 1-5.

The acid addition salts are usually obtained in a conventional manner by mixing the free base or solutions thereof with the appropriate acid or solutions thereof in an organic solvent, for example a lower alcohol such as methanol, ethanol or propanol, or a lower ketone such as acetone, methyl ethyl ketone or methyl isobutyl ketone, or an ether such as diethyl ether, tetrahydrofuran or dioxane. It is possible to use mixtures of the said solvents to improve the crystallization. Furthermore, it is possible to prepare pharmaceutically acceptable aqueous solutions of acid addition compounds of the amino compounds of the formula I by dissolving the free bases in an aqueous acid solution.

The compounds according to the invention and the salts thereof with physiologically tolerated acids have valuable pharmacological actions. In particular, they inhibit gastrointestinal $K^+/H^+$ ATPase and gastric acid secretion. The compounds according to the invention can therefore be used for the therapy of all disorders in which a reduction in gastric acid secretion has a beneficial effect on healing, eg. gastric or duodenal ulcer, gastritis, reflux esophagitis, and Zollinger-Ellison syndromes (cf. Review on Inhibitors of $K^+/H^+$ ATPase, G. Sachs et al., Ann. Rev. Pharmacol Toxicol. 28 (88) 269-284 and literature cited therein).

The present invention also relates to drugs for oral, rectal or intravenous administration, which, besides conventional carriers and diluents, contain the compounds of the formula I or acid addition salts thereof as active compound, and to the use of the novel compounds and the physiologically tolerated salts thereof for the treatment of the said disorders.

The drugs of the present invention are prepared in a conventional manner with a suitable dosage using the customary solid or liquid carriers or diluents and the auxiliaries customarily used in pharmaceutical technology according to the desired mode of administration. The preferred forms are suitable for oral administration. Examples of such forms are uncoated, film- and sugar-coated tablets, capsules, pills, powders, solutions or suspensions, or depot forms.

Also suitable are, of course, parenteral forms such as solutions for injection. Suppositories are another example.

Appropriate tablets can be obtained, for example, by mixing the active compound with known auxiliaries, for example inert diluents such as dextrose, sugar, sorbitol, mannitol, polyvinyl pyrrolidone, disintegrants such as corn starch or alginic acid, binders such as starch or gelatin, lubricants such as magnesium stearate or talc and/or agents to achieve a depot effect such as carboxypolymethylene, carboxymethylcellulose, cellulose acetate phthalate or polyvinyl acetate. The tablets can also be composed of several layers.

Coated tablets can be produced by coating cores produced in a similar manner to the tablets with customary coating agents, for example polyvinyl pyrrolidone or shellac, gum arabic, talc, titanium dioxide or sugar. It is also possible for the coating to be composed of several layers, and for the auxiliaries mentioned above for the tablets to be used.

Solutions or suspensions containing the active compound according to the invention can additionally contain agents to improve the flavor, such as saccharin, cyclamate or sugar, and, for example, flavorings such as vanillin or orange extract. They can also contain suspension auxiliaries such as sodium carboxymethylcellulose or preservatives such as p-hydroxybenzoates. Capsules containing active substances can be produced, for example, by the active substance being mixed with an inert carrier such as lactose or sorbitol and encapsulated in gelatin capsules.

Suitable suppositories can be produced, for example, by mixing with carriers intended for this purpose, such as neutral fats or polyethylene glycol or derivatives thereof.

A single dose for humans on oral or rectal administration is from 10 to 1000 mg, and on i.v. administration is from 0.01 to 1.0 mg/kg of body weight.

The following design of test has been used to determine the action of the compounds according to the invention: The mucosa from a freshly removed pig stomach is homogenized in 0.25 M sucrose, 20 mM Tris (tris(hydroxymethyl)aminomethane), 1 mM EGTA (ethylenebis(oxyethylenenitrilo)tetraacetic acid) pH 7.0 in an ice bath and centrifuged at 20 000 ×g for 20 min. The supernatant is centrifuged at 100 000 ×g for 60 min. The resulting microsomal pellet is homogenized with 50 mN Tris+2 mM $MgCl_2$+0.1 mM EGTA, pH 7.5, and frozen in portions at −20° C. The $K^+/H^+$ ATPase activity is assayed in 1 ml mixtures of the following composition: 50 mM Tris/HCl buffer, pH 7.5, 2 mM $MgCl_2$, 20 μg of membrane protein with or without addition of 5 mM KCl. The ATPase reaction is started by addition of $Na_2ATP$, final concentration 2 mM, reaction time 15 min at 37° C. The reaction is then stopped by addition of 1 ml of 20% trichloroacetic acid. The liberated phosphate is determined by the method of Sanui (Analyt. Biochem. 60 (1974), 489–504).

Addition of the compounds according to the invention in the above design of test inhibits $K^+/H^+$ ATPase. Examples 1 to 11, compounds of the general formula I, $R^1 = CH_3$, $R^5 = CH_3O$, $R^6 = H$ General procedure:

A mixture of 1 equivalent of 4-chloro-8-methoxy-2-methylquinoline, 1 to 11 equivalents of an amine of the formula $R^2CH_2NH_2$ and 5 to 20 equivalents of phenol was heated at 110 to 140° C., in an autoclave if necessary, for 3 to 8 hours. After cooling, ethyl acetate was added to the reaction mixture which was then extracted several times with aqueous tartaric acid solution. The aqueous phase was made alkaline with concentrated NH, or dilute NaOH. This resulted in crystallization of part of the desired product, and the crystals were filtered off with suction, washed with water, ether or ethyl acetate, dried and boiled with ether. Filtration with suction and drying resulted in the compounds according to the invention. If no crystals separated out of the alkaline aqueous phase it was extracted several times with ethyl acetate, and the organic phase was washed several times with dilute NaOH and $H_2O$, dried over $Na_2SO_4$ and freed of solvent in a rotary evaporator. The crude products were boiled with ether, and the product was filtered off with suction and dried. If necessary, the products were recrystallized from, for example, isopropanol or ethanol (see table).

The compounds of Examples 1 to 11 were obtained by this procedure.

TABLE 1

| | Compounds of the formula I, $R^1 = CH_3$, $R^5 = CH_3O$, $R^6 = H$ | | | | | | (I) |
| Ex. | $R^2$ | Equiv. of $R^2CH_2NH_2$ | Equiv. of phenol | Reaction cond. (h) | T (°C.) | Yield (%) | m.p. (°C.) |
| --- | --- | --- | --- | --- | --- | --- | --- |
| 1 | $CH_3$ 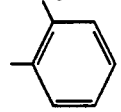 | 11 | 20 | 4 | 130 | 36 | 228–229[a)] |
| 2 | $CH_3O$ 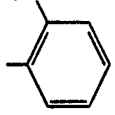 | 11 | 15 | 3 | 130 | 40 | 223–224[b)] |
| 3 | $C_2H_5$ 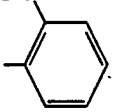 | 1.5 | 5 | 4 | 140 | 69 | 208–209[a)] |

TABLE 1-continued

Compounds of the formula I,
$R^1 = CH_3$, $R^5 = CH_3O$, $R^6 = H$ (I)

| Ex. | $R^2$ | Equiv. of $R^2CH_2NH_2$ | Equiv. of phenol | Reaction cond. (h) | T (°C.) | Yield (%) | m.p. (°C.) |
|---|---|---|---|---|---|---|---|
| 4 | Br-phenyl | 1.5 | 15 | 4 | 140 | 88 | 250–251[a] |
| 5 | naphthyl | 1.5 | 15 | 4 | 130 | 75 | 275–276[a] |
| 6 | 2,3-dichlorophenyl | 1.5 | 15 | 8 | 150 | 84 | 259–260[a] |
| 7 | 2,6-dimethoxyphenyl ($CH_3O$, $CH_3O$) | 1.1 | 11 | 6 | 140 | 31 | 269–270[a] |
| 8 | 2,5-dimethylphenyl ($CH_3$, $CH_3$) | 1.1 | 11 | 6 | 140 | 11 | 286–287[a] |
| 9 | 2,6-dimethylphenyl ($CH_3$, $CH_3$) | 1.0 | 11 | 6 | 140 | 27 | 240–241[b] |
| 10 | 2,4-dimethylphenyl ($CH_3$, $CH_3$) | 1.5 | 15 | 4 | 140 | 51 | 208–209[a] |
| 11 | 2,5-dimethylphenyl ($CH_3$, $CH_3$) | 1.5 | 15 | 6 | 140 | 64 | 230–231[a] |

[a] recrystallized from ethanol
[b] recrystallized from isopropanol

Examples 12a–12d, compounds of the general formula I, $R^1 = CH_3$, $R^5 = CH_3O$, $R^6 = H$.

The compounds 12(a)–12(d) were obtained by reaction of 4-chloro-8-methoxy-2-methylquinoline with amines $R^2CH_2NH_2$ similar to the general procedure for Examples 1 to 11.

EXAMPLE 12(a)

4-(2-Chlorobenzylamino)-8-methoxy-2-methylquinoline (melting point 230–231° C.).

EXAMPLE 12(b)

4-(2-fluorobenzylamino)-8-methoxy-2-methylquinoline melting point: 248–249° C.

EXAMPLE 12(c)

4-(2-chloro-6-fluorobenzylamino)-8-methoxy-2-methylquinoline. melting point: 259–260° C.

EXAMPLE 12(d)

4-(2,6-difluorobenzylamino)-8-methoxy-2-methylquinoline. melting point: 258–259° C.

Example 13, compound of the general formula I, $R^1=CH_3$, $R^2=$1-naphthyl, $R^5=CH_3O$, $R^6=H$ a) 8-Methoxy-2-methyl-4-phenoxyquinoline compound of the formula II, $R^1=CH_3$, $X=OC_6H_5$, $R^5=CH_3O$, $R^6=H$ 10 g (=48.2 mmol) of 4-chloro-8-methoxy-2-methylquinoline and 30 g (=319 mmol) of phenol in 80 ml of concentrated ammonia solution were maintained at 140° C. in an autoclave for 8 hours. The mixture was diluted with ethyl acetate, and the organic phase was washed several times with tartaric acid solution The aqueous phase was then adjusted to pH 10 with NaOH and extracted with ethyl acetate. The organic phase was dried over sodium sulfate, the solvent was removed in a rotary evaporator, the residue was stirred with ether, and the product was filtered off with suction. 8.4 g (=93%) of the abovementioned compound of melting point 140–141° C. were obtained.

b) 8-Methoxy-2-methyl-4-(1-naphthylmethylamino)quinoline compound of the general formula I, $R^1=CH_3$, $R^2=$1-naphthyl, $R^5=CH_3O$, $R^6=H$ 2.0 g (=7.55 mmol) of 8-methoxy-2-methyl-4-phenoxyquinoline, 1.8 g (=11.5 mmol) of lamine and 7.1 g (=75 mmol) of phenol were maintained at 130° C. in an autoclave for 5 hours. After cooling, ethyl acetate was added to the reaction mixture which was then extracted several times with tartaric acid solution. The aqueous phase was made alkaline with concentrated ammonia solution, and the precipitated product was filtered off with suction, washed with ether and dried. 1.6 g (=65%) of 8-methoxy-2-methyl-4-(1-naphthylmethylamino)quinoline, which was identical to the compound from Example 5, were obtained.

Example 14, compound of the general formula I, $R^1=CH_2OH$, $R^2=$o-tolyl, $R^5=CH_3O$, $R^6=H$ a) Methyl 4 TM chloro-8-methoxyquinoline-2-carboxylate compound of the formula V, $R^5=CH_3O$, $R^6=H$, $R^8=CH_3$ 57.6 g (247 mmol) of methyl 4-hydroxy-8-methoxyquinolinecarboxylate were introduced a little at a time into 113 ml of $POCl_3$ at room temperature to 40° C., and the mixture was heated at 80° C. for 2 hours. The dark reaction mixture was poured onto ice and adjusted to pH 6 with concentrated $K_2CO_3$ solution. The precipitate was filtered off with suction and recrystallized from DMF/water. 42.7 g (=69%) of methyl 4-chloro-8-methoxyquinoline-2-carboxylate of melting point 139–141° C. were obtained.

b) 8(Methoxy-4-(2-methylbenzylamino)quinoline-2-carboxylic acid, compound of the formula III, $R^2=$o-tolyl, $R^5=CH_3O$, $R^6=R^7=H$ A mixture of 54 g (=215 mmol) of methyl 4-chloro-8-methoxyquinoline-2-carboxylate, 33.7 g (=278 mmol) of 2-methylbenzylamine and 243 g (=2.58 mmol) of phenol was heated at 140° C. in an autoclave for 4 hours. The cooled reaction mixture was added dropwise to 4 l of ethyl acetate, and the resulting precipitate was filtered off with suction. The solid was dissolved in 1 l of THF and the pH was adjusted to 10 with 10% NaOH. The mixture was stirred at 50° C. for 1 hour, maintaining the pH constant, cooled to 10° C. and adjusted to pH 5-6 with dilute HCl. This resulted in the product crystallizing. 18.85 g of 8-methoxy-4-(2-methylbenzylamino)quinoline-2-carboxylic acid of melting point 276–277° C. were obtained.

c) 2-Hydroxymethyl-8-methoxy-4-(2-methylbenzylamino)quinoline, compound of the formula I, $R^1=CH_2OH$, $R^2=$o-tolyl, $R^5=CH_3O$, $R^6=H$ A mixture of 0.50 g (12.9 mmol) of LiAlH , 2.8 g (8.6 mmol) of 8-methoxy-4-(2-methylbenzylamino)quinoline-2-carboxylic acid and 20 ml of absolute THF were reacted at room temperature under $N_2$ for 6 hours. 3.6 ml of ethyl acetate, 36 ml of water and 17 ml of 2 N NaOH were successively added. After standing overnight, the filtrate was concentrated in a rotary evaporator, Water was added, and the mixture was extracted with ethyl acetate. After drying over $Na_2SO_4$, the ethyl acetate was removed in a rotary evaporator, and the residue was dissolved in methanol and acidified with methanolic HCl solution. Removal of the solvent in a rotary evaporator and recrystallization from ethanol yielded 2.69 g (=81%) of 2-hydroxymethyl -8-methoxy-4-(2-methylbenzylamino)-quinoline hydrochloride of melting point 158–160° C. Example 15, compound of the formula I, $R^1=CH_3OCH_2$, $R^2=$o-tolyl, $R^5=CH_3O$, $R^6=H$ a) 2-Chloromethyl-8-methoxy-4-(2-methylbenzylamino)quinoline hydrochloride compound of the formula IV, $R^2=$o-tolyl, $R^5=CH_3O$, $R^6=H$ A mixture of 2 5 g (=7.2 mmol) of 2-hydroxymethyl-8-methoxy-4-(2-methylbenzylamino)quinoline hydrochloride, 5.3 ml of thionyl chloride and 2 drops of DMF was stirred at room temperature for 90 minutes. The mixture was poured onto ice, made alkaline with 1 N NaOH and extracted with ethyl acetate. The crude product after the organic phase had been dried with $Na_2SO_4$ and the solvent had been stripped off was converted into the hydrochloride with methanolic hydrochloric acid. 2.48 g of 2-chloromethyl-8-methoxy-4-(2-methylbenzylamino)quinoline hydrochloride were obtained.

b) 8-Methoxy-2-methoxymethyl-4-(2-methylbenzylamino)quinoline compound of the formula I, $R^1=CH_3OCH_2$, $R^2=$o-tolyl, $R^5=CH_3O$, $R^6=H$ 800 mg (=2.2 mmol) of 2-chloromethyl-8-methoxy-4(2-methylbenz-ylamino)quinoline hydrochloride were refluxed with 1.2 g (=22 mmol) of sodium methylate in 30 ml of absolute methanol for 5 hours The mixture was concentrated in a rotary evaporator, ethyl acetate was added, and the mixture was extracted several times with $K_2CO_3$ solution. The residue after drying over $Na_2SO_4$ and removal of the solvent was recrystallized from ethanol 200 mg (=28%) of 8-methoxy..2-methoxymethyl-4-(2-methylbenzylamino)quinoline of melting point 194-195° C. were obtained Example 16, 4-chloro-8-methoxy-2-methoxymethylquinoline, formula II, $R^1=CH_3OCH_2$, $R^5=CH_3O$, $X=Cl$, $R^6=H$ a) Methyl 3-(2-methoxyanilino)-4-methoxy-2-butenoate A mixture of 100 g of o-anisidine, 190 g of methyl γ-methoxyacetoacetate, 2.3 ml of acetic acid, 203 g of calcium sulfate and 800 ml of absolute ethanol was refluxed for 16 hours. The residue after filtration and concentration of the filtrate under reduced pressure was taken up in ethyl acetate, the solution was extracted several times with 2 N NaOH and 5% strength citric acid solution and dried over $Na_2SO_4$, and the solvent was removed in a rotary evaporator. 150 g of crude product were obtained and were employed without further purification in the following stage.

b) 4-Hydroxy-8-methoxy-2-methoxymethylquinoline 150 g of the crude product from Example 16a) were stirred in 330 g of polyphosphoric acid at 80° C. for 4 hours. 1 l of $H_2O$ was added to the mixture, and the pH was adjusted to 6 with concentrated NaOH. o-Anisidine was removed with extraction with ethyl acetate. The aqueous phase was saturated with NaCl and then the desired product was extracted with $CH_2Cl_2$. Drying over $Na_2SO_4$ and stripping off the solvent were followed by recrystallization from ethyl acetate. 60 g of 4-hydroxy-8-methoxy-2-methoxymethylquinoline of melting point 193-195° C. were obtained.

c) 4-Chloro-8-methoxy-2-methoxymethylquinoline, compound II, $R^1=CH_3OCH_2$, $R^5=CH_3O$, $R^6=H$, $X=Cl$ 60 g of the compound from Example 16b) were stirred with 210 g of $POCl_3$ at room temperature for 1 hour and under reflux for 1 hour. The mixture was cooled and poured into 800 ml of ice and, while cooling, the mixture was made alkaline with concentrated NaOH. The aqueous phase was saturated with NaCl and then extracted with $CH_2Cl_2$. The crude product after drying over $Na_2SO_4$ and removal of the solvent in a rotary evaporator was purified by column chromatography ($SiO_2$, mobile phase: ethyl acetate). 26 g of 4-chloro-8-methoxy-2-methoxymethylquinoline of melting point 67-69° C. were obtained Example 17, compounds of the general formula I, $R^1=CH_3OCH_2$, $R^5=CH_3O$, $R^6=H$ The compounds of Examples 17a) to 17e) were obtained by reacting the compound from Example 16c) with amines $R^2CH_2NH_2$ and phenol at 120 to 130° C. by the general procedure of Examples 1 to 11.

EXAMPLE 17(a)

8-Methoxy-2-methoxymethyl-4-(2-methylbenzylamino)quinoline, melting point 194-195° C.

EXAMPLE 17(b)

4-(2-Bromobenzylamino)-8-methoxy-2-methoxymethylquinoline melting point 202-203° C.

EXAMPLE 17(c)

4-(2-Chlorobenz-ylamino)-8-methoxy-2-methoxymethylquinoline. melting point 213-214° C.

EXAMPLE 17(d)

8-Methoxy-4-(2-methox-ybenzylamino)-2-methoxymethylquinoline. melting point 207-208° C.

EXAMPLE 17(e)

8-Methoxy-2-methoxymethyl-4-(1-naphthylmethylamino)quinoline. melting point 211-212° C. The following examples can be obtained by reacting the appropriate compounds of the general formula II with the amines $R^2CH_2NH_2$ in a similar manner to the general procedure for Examples 1 to 11.

Example 18, compounds of the general formula I,

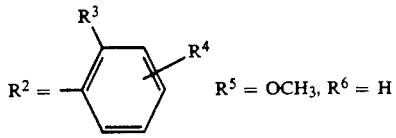

$R^5 = OCH_3$, $R^6 = H$

| Ex. | $R^1$ | $R^3$ | $R^4$ | m.p. [°C.] |
|---|---|---|---|---|
| 18a | $CH_3$ | $CF_3$ | H | 126-128 |
| 18b | $CH_3$ | $iC_3H_7$ | H | |
| 18c | $C_2H_5$ | Br | H | |
| 18d | $C_2H_5$ | $CH_3$ | H | |
| 18e | $C_2H_5$ | $OCH_3$ | H | |
| 18f | $nC_3H_7$ | Cl | H | |
| 18g | $nC_3H_7$ | Cl | 6-F | |
| 18h | $iC_3H_7$ | $CH_3$ | H | |
| 18i | $iC_3H_7$ | Br | H | |
| 18j | $CH_2OH$ | Br | H | |
| 18k | $CH_2OH$ | Cl | H | |
| 18l | $CH_2OH$ | Cl | 6-Cl | |
| 18m | $CH_2OH$ | $OCH_3$ | H | |
| 18n | $CH_2OC_2H_5$ | $CH_3$ | H | |
| 18o | $CH_2OC_2H_5$ | Br | H | |
| 18p | $CH_2OC_2H_5$ | Cl | H. | |
| 18q | $CH_2OiC_3H_7$ | $OCH_3$ | H | |

Example 19, compounds of the general formula I,

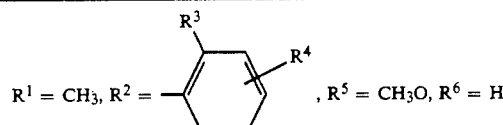

$R^1 = CH_3$, $R^5 = CH_3O$, $R^6 = H$

| Ex. | $R^3$ | $R^4$ | m.p. [°C.] |
|---|---|---|---|
| 19a | $CH_3$ | 4-OH | |
| 19b | Br | 4-OH | |
| 19c | Cl | 4-OH | |
| 19d | Br | 4-F | 226-227 |
| 19e | $nC_3H_7$ | H | |
| 19f | $CH_2OH$ | H | |
| 19g | $CH_2OCH_3$ | H | |
| 19h | $OC_2H_5$ | H | |
| 19i | $O-nC_3H_7$ | H | |
| 19j | $O-iC_3H_7$ | H | |
| 19k | $OCH_3$ | 6-F | |
| 19l | $OCH_3$ | 6-Cl | |

Example 20, compounds of the general formula I

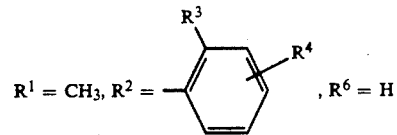

$R^1 = CH_3$, $R^6 = H$

| Ex. | $R^3$ | $R^4$ | $R^5$ |
|---|---|---|---|
| 20a | $CH_3$ | H | $OC_2H_5$ |
| 20b | Br | H | $OC_2H_5$ |
| 20c | $OCH_3$ | H | $OC_2H_5$ |
| 20d | Cl | H | $OC_2H_5$ |

-continued

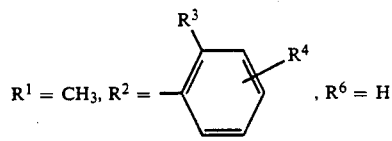

| Ex. | R³ | R⁴ | R⁵ |
|---|---|---|---|
| 20e | Cl | 6-F | OC₂H₅ |
| 20f | Br | H | O-nC₃H₇ |
| 20g | CH₃ | H | O-nC₃H₇ |
| 20h | CH₃ | H | CH₂OH |
| 20i | Br | H | CH₂OH |
| 20j | Cl | H | CH₂OH |
| 20k | OCH₃ | H | CH₂OH |
| 20l | CH₃ | H | CH₂OCH₃ |
| 20m | Br | H | CH₂OCH₃ |
| 20n | Cl | H | CH₂OCH₃ |
| 20o | OCH₃ | H | CH₂OCH₃ |
| 20p | CH₃ | H | CH₂OC₂H₅ |
| 20q | Br | H | CH₂OiC₃H₇ |
| 20r | CH₃ | H | OH |
| 20s | Br | H | OH |
| 20t | Cl | H | OH |
| 20u | OCH₃ | H | OH |
| 20v | Br | 4-OH | OH |
| 20w | CH₃ | H | F |
| 20x | OCH₃ | H | F |
| 20y | Br | H | F |
| 20z | Cl | H | F |
| 2a | CH₃ | H | Cl |
| 2b | OCH₃ | H | Cl |
| 2c | Br | H | Cl |
| 2d | Cl | H | Cl |
| 2e | OCH₃ | H | Br |
| 2f | CH₃ | H | Br |
| 2g | Br | H | Br |
| 2h | Cl | H | Br |

Example 21, compounds of the general formula I,

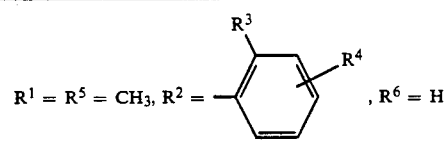

| Ex. | R³ | R⁴ |
|---|---|---|
| 21a | CH₃ | H |
| 21b | CH₃ | 6-CH₃ |
| 21c | Cl | 6-Cl |
| 21d | Cl | 6-F |
| 21e | Cl | H |
| 21f | Br | H |
| 21g | Br | 6-Cl |
| 21h | C₂H₅ | H |
| 21i | CH₂OH | H |
| 21j | CH₂OCH₃ | H |
| 21k | OCH₃ | H |
| 21l | OCH₃ | 6-OCH₃ |
| 21m | OCH₃ | 6-Cl |
| 21n | OC₂H₅ | H |
| 21o | F | 6-F |

Example 22, compounds of the general formula I,

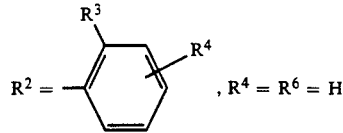

| Ex. | R² | R³ | R⁵ |
|---|---|---|---|
| 22a | CH₂OH | CH₃ | CH₃ |
| 22b | CH₂OCH₃ | CH₃ | CH₃ |
| 22c | CH₂OCH₃ | Br | CH₃ |
| 22d | CH₂OCH₃ | OCH₃ | CH₃ |
| 22e | CH₂OCH₃ | Cl | CH₃ |
| 22f | CH₂OH | Cl | C₂H₅ |
| 22g | CH₂OCH₃ | Br | C₂H₅ |
| 22h | CH₃ | CH₃ | C₂H₅ |
| 22i | CH₃ | Br | C₂H₅ |
| 22j | CH₃ | Cl | C₂H₅ |
| 22k | CH₃ | OCH₃ | C₂H₅ |
| 22l | CH₃ | CH₃ | i-C₃H₇ |
| 22m | CH₃ | Br | n-C₃H₇ |
| 22n | CH₃ | OCH₃ | n-C₃H₇ |

Example 23, compounds of the general formula I,

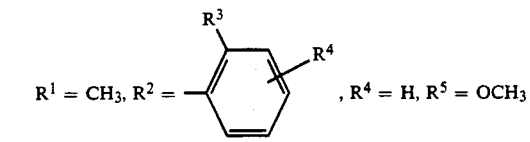

| Ex. | R³ | R⁶ |
|---|---|---|
| 23a | CH₃ | 6-OCH₃ |
| 23b | Br | 6-OCH₃ |
| 23c | Cl | 6-OCH₃ |
| 23d | OCH₃ | 6-OCH₃ |
| 23e | CH₃ | 5-OCH₃ |
| 23f | Br | 5-OCH₃ |
| 23g | Cl | 5-OCH₃ |
| 23h | CH₃ | 5-CH₃ |
| 23i | OCH₃ | 5-CH₃ |
| 23j | Br | 5-CH₃ |
| 23k | CH₃ | 7-Br |
| 23l | Br | 7-Br |
| 23m | CH₃ | 7-Cl |
| 23n | CH₃ | 5-Cl |
| 23o | OCH₃ | 5-Cl |
| 23p | Br | 5-Cl |
| 23q | Br | 5-Br |
| 23r | Cl | 5-Br |
| 23s | OCH₃ | 5-Br |
| 23t | CH₃ | 5-Br |

We claim:
1. A 2-alkyl-4-arylmethylaminoquinoline of the formula

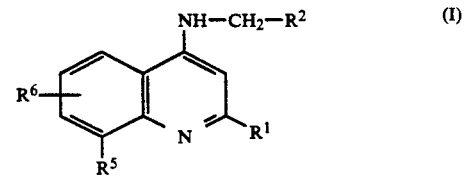

where
$R^1$ is $C_1-C_3$-alkyl which can be substituted by hydroxyl or $C_1-C_3$-alkoxy,
$R^2$ is either naphthyl or a radical of the formula (a)

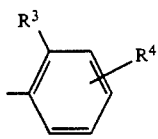

where
- $R^3$ is $C_1$-$C_3$-alkyl which can be substituted by hydroxyl or methoxy, or is $C_1$-$C_3$-alkoxy, fluorine, chlorine or bromine, and
- $R^4$ is hydrogen, 6-methyl, 4-hydroxy, 6-methoxy, 6-fluoro or 6-chloro, and
- $R^5$ is $C_1$-$C_3$-alkoxy,
- $R^6$ is hydrogen, and the physiologically tolerated salts thereof.

2. A compound as claimed in claim 1, where $R^5$ is methoxy, and the physiologically tolerated salts thereof.

3. A compound as claimed in claim 2 wherein $R^1$ is methyl which can be substituted by hydroxy or $C_1$-$C_3$-alkoxy, and the physiologically tolerated salts thereof.

4. A compound as claimed in claim 2 wherein $R^1$ is methyl, methoxymethyl or hydroxymethyl, $R^2$ is the group (a), where $R^3$ is methyl, ethyl, methoxy, chlorine or bromine, and $R^4$ is a hydrogen or 6-fluoro or 6-chloro and $R^5$ is methoxy, and the physiologically tolerated salts thereof.

5. A pharmaceutical composition for oral or rectal use, which contains as active compound 10 to 1000 mg of a compound of the formula I as claimed in claim 1 per single dose, besides conventional pharmaceutical auxiliaries.

6. A pharmaceutical composition for intravenous administration, which contains as active compound 0.01 to 1 mg/kg of body weight of a compound of the formula I as claimed in claim 1, besides conventional pharmaceutical auxiliaries.

7. A pharmaceutical composition for disorders in which a reduction in gastric acid secretion has a beneficial effect on healing, which contains as active compound an effective amount of a compound of the formula I as claimed in claim 1, besides conventional pharmaceutical auxiliaries.

* * * * *